United States Patent [19]
Schmid et al.

[11] Patent Number: 6,018,056
[45] Date of Patent: Jan. 25, 2000

[54] INTERMEDIATES AND PROCESSES FOR PREPARING BENZO (B) THIOPHENES

[75] Inventors: Christopher Randall Schmid; Jerry Wayne Misner, both of Indianapolis, Ind.

[73] Assignee: Eli Lilly and Company, Indianapolis, Ind.

[21] Appl. No.: 09/069,278

[22] Filed: Apr. 29, 1998

Related U.S. Application Data

[60] Provisional application No. 60/045,131, Apr. 30, 1997.

[51] Int. Cl.$^7$ .................. C07D 327/00; C07D 333/52
[52] U.S. Cl. .................................................. 549/2; 549/51
[58] Field of Search ............................................. 549/2, 51

[56] References Cited

U.S. PATENT DOCUMENTS

| | | | |
|---|---|---|---|
| 3,394,125 | 7/1968 | Crenshaw | 260/326.5 |
| 3,413,305 | 11/1968 | Crenshaw | 760/326.5 |
| 4,133,814 | 1/1979 | Jones et al. | 260/326 |
| 4,358,593 | 11/1982 | Jones et al. | 546/202 |
| 4,380,635 | 4/1983 | Peters | 546/202 |
| 4,418,068 | 11/1983 | Jones et al. | 424/267 |
| 5,223,510 | 6/1993 | Gubin et al. | 514/299 |
| 5,395,842 | 3/1995 | Labrie et al. | 514/320 |
| 5,470,854 | 11/1995 | Angerer et al. | 514/233 |
| 5,472,962 | 12/1995 | Sagamihara et al. | 514/233.5 |
| 5,482,949 | 1/1996 | Black et al. | 514/324 |
| 5,552,412 | 9/1996 | Cameron et al. | 514/317 |
| 5,629,425 | 5/1997 | Labell et al. | 546/202 |

FOREIGN PATENT DOCUMENTS

| | | |
|---|---|---|
| 0062503 | 10/1982 | European Pat. Off. . |
| 0062504 | 10/1982 | European Pat. Off. . |
| 605 193 | 7/1994 | European Pat. Off. . |
| 2097392 | 4/1982 | United Kingdom . |
| 2096608 | 10/1982 | United Kingdom . |
| 2097788 | 11/1982 | United Kingdom . |
| WO93/10741 | 6/1993 | WIPO . |
| WO95/10513 | 4/1995 | WIPO . |

OTHER PUBLICATIONS

Lonley et al. Chemical abstract vol. 88 No. 177, 168, "Thianayhten–>–one Chemistry", 1976.
Jones, C.D., et al, *J. Med. Chem.* 27(8) 1057–1066 (1971).
Romeo Wagner, *Synthetic Organic Chemistry*, (171–172) 1953.
Jones, C.D., et al *J. Med Chem.* 35(5) 931–938 1992.
Kym, R.P. et al, *J. Med, Chem.*, 36 (24), 3911–3921 1993.
Jackson, T.G., et al *J. Chem. Soc.* 1728–1729 (1969).
Kametani, et al *J. Org. Chem.* 41 (15) 2545–2547 (1976).
Crenshaw, R.R., et al *J. Med. Chem.* 14(12) 1185–1190 (1971).

*Primary Examiner*—John Kight
*Assistant Examiner*—Raymond Covington
*Attorney, Agent, or Firm*—Gilbert T. Voy

[57] ABSTRACT

The instant invention provides processes for preparing compounds of formula IV, V, and IX, having the structures provided hereinbelow:

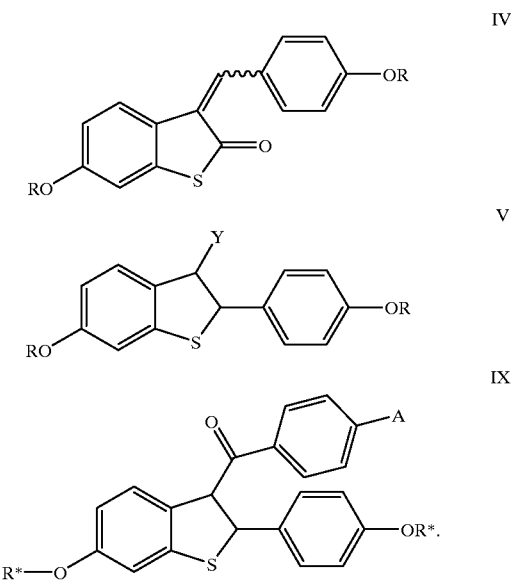

These compounds are useful intermediates in the further preparation of benzo[b] thiophenes.

13 Claims, No Drawings

INTERMEDIATES AND PROCESSES FOR PREPARING BENZO (B) THIOPHENES

This application claims benefit of provisional application 60/045,131, filed Apr. 30, 1997.

TECHNICAL FIELD

The present invention relates to pharmaceutical chemistry. More particularly, the present invention relates to pharmaceutical intermediates and processes for preparing and using said intermediates.

BACKGROUND OF THE INVENTION

The compound 6-hydroxy-2-(4-hydroxyphenyl)-3-[4-(2-piperidinoethoxy)benzoyl]benzo[b]thiophene, or raloxifene, is an important member of the class of compounds known as selective estrogen receptor modulators(SERMs). That compound is disclosed and claimed in U.S. Pat. No. 4,418,068.

Several methods of preparing benzo[b]thiophenes including raloxifene, have previously been disclosed (See, for example, U.S. Pat. Nos. 4,133,814, 4,358,593, 4,380,635, 5,523,416, 5,554,755, 5,606,075, and 5,606,076). In the event that the starting materials or the reagents necessary for the processes described in the aforementioned U.S. patents become scarce or unavailable, it would be advantageous to have alternative commercial processes for the preparation of benzo[b]thiophenes. The present invention provides both intermediates and synthetic routes for preparing the intermediates, and for preparing substituted benzo[b] thiophenes therefrom.

SUMMARY OF THE INVENTION

The present invention provides compounds of formula IV

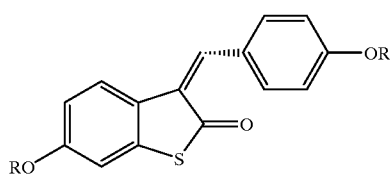

IV wherein R at each occurrence is independently a hydroxy protecting group.

The present invention further provides compounds of formula V

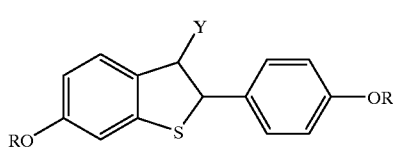

V wherein Y is —$CO_2R^1$, —CO-halo, —CONMe(OMe), —$CONH_2$, or cyano, and $R^1$ is hydrogen or $C_1$-$C_4$ alkyl.

The present invention further provides compounds of formula IX

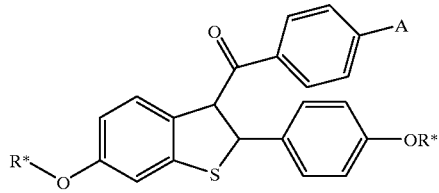

IX wherein A is hydroxy, halo, nitro, $C_1$-$C_4$ alkoxy, —O—$(CH_2)_2$-halo, or —O—$(CH_2)_2$—$NR^2R^3$; and $R^*$ is at each occurrence is independently a hydroxy protecting group or hydrogen; and $R^2$ and $R^3$ are independently $C_1$-$C_4$ alkyl, or combine to form, together with the nitrogen atom to which they are attached,a pyrrolidinyl, piperidinyl, morpholino, or hexamethyleneimino ring.

The present invention also provides processes for preparing compounds of formula X

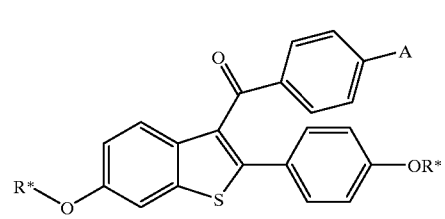

X wherein A is hydroxy, halo, nitro, $C_1$-$C_4$ alkoxy, —O—$(CH_2)_2$-halo, or —O—$(CH_2)_2$—$NR^2R^3$,$R^*$ is at each occurrence independently a hydroxy protecting group or hydrogen, and $R^2$ and $R^3$ are independently $C_1$-$C_4$ alkyl, or combine to form, together with the nitrogen atom to which they are attached, a pyrrolidinyl, piperidinyl, morpholino, or hexamethyleneimino ring.

DETAILED DESCRIPTION OF THE INVENTION

The present invention further provides processes for preparing compounds of formula IV

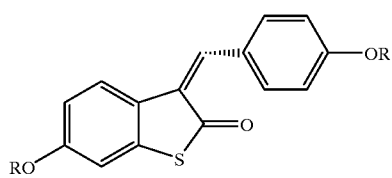

IV wherein R is independently at each occurrence a hydroxy protecting group, which includes reacting a compound of formula II

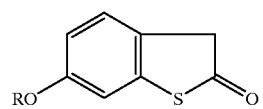

II with a compound of formula III

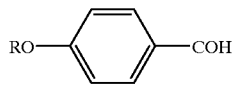

in the presence of a suitable base.

The present invention still further provides processes for preparing a compound of formula V

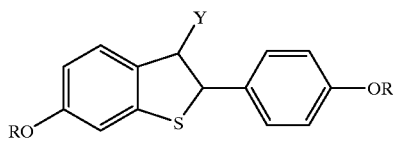

wherein Y is —$CO_2R^1$, —CO-halo, —CONMe(OMe), —$CONH_2$, or cyano, $R^1$ is hydrogen or $C_1$-$C_4$ alkyl, which includes reacting a compound of formula IV with a lower alcohol in the presence of a suitable base.

The present invention further provides a process for preparing a compound of formula X

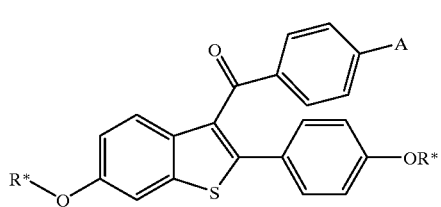

wherein A is hydroxy, halo, nitro, $C_1$-$C_4$ alkoxy, —O—$(CH_2)_2$-halo, or —O—$(CH_2)_2$—$NR^2R^3$, $R^*$ is independently at each occurrence a hydroxy protecting group or hydrogen, and $R^2$ and $R^3$ are independently $C_1$-$C_4$ alkyl, or combine to form, together with the nitrogen atom to which they are attached, a pyrrolidinyl, piperidinyl, morpholino, or hexamethyleneimino ring, which includes acylating a compound of formula VI

wherein M is hydrogen, lithium, magnesium chloride, magnesium bromide, or magnesium iodide, with a compound of formula Vg

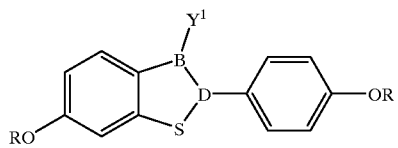

wherein B—D is —CH—CH— or —C=C—, R is independently at each occurrence a hydroxy protecting group, and $Y^1$ is —$CO_2R^1$, —CO-halo, —CONMe(OMe), or cyano, in the presence of a Lewis acid catalyst in the case where M is hydrogen and $Y^1$ is —CO-halo.

As used throughout this specification and the appended claims, the terms employed have the meanings ascribed to them in the art. The term "$C_1$-$C_4$ alkyl" refers to a straight or branched alkyl chain having from one to four carbon atoms. Typical $C_1$-$C_4$ alkyl groups include methyl, ethyl, propyl, isopropyl, n-butyl, t-butyl, and isobutyl. The term "$C_1$-$C_6$ alkyl" refers to a straight or branched alkyl chain having from one to six carbon atoms. Typical $C_1$-$C_6$ alkyl groups include those described for $C_1$-$C_4$ alkyl in addition to pentyl, 2-methylbutyl, hexyl, 2-methylhexyl, 3-methylhexyl, and the like. The term "lower alcohols" refers to $C_1$-$C_4$ alcohols including methanol, ethanol, propanol, isopropanol, butanol, n-butanol, isobutanol, tbutanol, and the like. The term "$C_1$-$C_4$ alkoxy" refers to a straight or branched alkyl chain having from one to four carbon atoms attached to an oxygen atom. Typical $C_1$-$C_4$ alkoxy groups include methoxy, ethoxy, propoxy, isopropoxy, n-butoxy, t-butoxy, and isobutoxy. The term "optionally substituted phenyl" refers to a phenyl group or a phenyl group substituted once or twice with $C_1$-$C_6$ alkyl, $C_1$-$C_4$ alkoxy, hydroxy, nitro, chloro, fluoro, or tri(chloro or fluoro)methyl. The term "halo" refers to fluorine, chlorine, bromine, and iodine.

The term "hydroxy protecting group" denotes a group understood by one skilled in the organic chemical arts of the type described in Chapter 2 of Protective Groups in Organic Synthesis, 2nd Edition, T. H. Greene, et al., John Wiley & Sons, New York, 1991, hereafter referred to as Greene. Such groups include, for example, ether groups, including methyl and substituted methyl ether groups, such as methyl ether, methoxymethyl ether, methylthiomethyl ether, tert-buylthiomethyl ether, (phenyldimethylsilyl)methoxymethyl ether, benzyloxymethyl ether, p-methoxy-benzyloxymethyl ether, and tert-butoxymethyl ether; substituted ethyl ether groups such as ethoxyethyl ether, 1-(2-chloroethoxy)ethyl ether, 2,2,2-trichloroethoxymethyl ether, and 2-(trimethylsilyl)ethyl ether; phenyl and substituted phenyl ether groups such as phenyl ether, p-chlorophenyl ether, p-methoxyphenyl ether, and 2,4-dinitrophenyl ether; benzyl and substituted benzyl ether groups such as benzyl ether, p-methoxybenzyl ether, onitrobenzyl ether, and 2,6-dichlorobenzyl ether; and alkylsilyl ether groups, such as trimethyl- triethyl- and triisopropylsilyl ethers, mixed alkyl-silyl ether groups such as dimethylisopropylsilyl ether, and diethylisopropylsilyl ether; and ester protecting groups of the general formula —CO—($C_1$-$C_6$) alkyl or —CO—Ar, where Ar is optionally substituted phenyl, or specific groups such as formate ester, benzylformate ester, mono- di- and trichloroacetate esters, phenoxyacetate ester, and p-chlorophenoxyacetate and the like. The species of hydroxy protecting group employed is not critical so long as the derivatized hydroxy group is stable to the condition of subsequent reaction(s) on other positions of the intermediate molecule and can be selectively removed at the appropriate point without disrupting the remainder of the molecule including any other hydroxy protecting group(s). Preferred protecting groups encompassed in this invention are methyl groups, for example where R or $R^*$ at each occurrence is methyl.

The term "fully aromatic" refers to a benzothiophene ring system where both of the rings together (phenyl and thiophene) are aromatic.

The term "Lewis acid catalyst" refers to the type of catalyst described in Olah, "Friedel-Crafts and Related Reactions," Interscience Publishing Co., New York, 1963 and includes metal halides such as aluminum bromide, aluminum chloride, boron trifluoride, boron trichloride, boron tribromide, titanium tetrachloride, titanium tetrabromide, stannic chloride, stannic bromide, bismuth trichloride, ferric chloride, and the like.

The term "suitable acid" refers to any acid reactive enough to effect the desired reaction without significantly effecting any undesired reactions. The skilled artisan will recognize that the reactivity of an acid relates to the ability to donate a proton (Bronsted acidity) or to the ability to accept an electron pair (Lewis acidity).

The term "suitable base" refers to any base reactive enough to effect the desired reaction without significantly effecting any undesired reactions. The skilled artisan will recognize that the reactivity of a base relates to the ability to donate a hydroxide ion (Bronsted basicity) or to the ability to donate an electron pair (Lewis basicity).

The term "suitable solvent" refers to any solvent which is inert to the ongoing reaction that sufficiently solubilizes the reactants to effect the desired reaction.

As mentioned above, the invention includes the pharmaceutically acceptable salts of compounds of formula V and VI. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the formula IX and X which are substantially non-toxic to living organisms. Typical pharmaceutically acceptable salts include those salts prepared by reaction of these compounds of the present invention with a mineral or organic acid. Such salts are known as acid addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

It should be recognized that the particular counterion forming a part of any salt of this invention is not of a critical nature, so long as the salt is pharmacologically acceptable and the counterion does not contribute any undesired qualities to the salt.

The compounds of formula IV occur in either the E or Z conformation, as shown below:

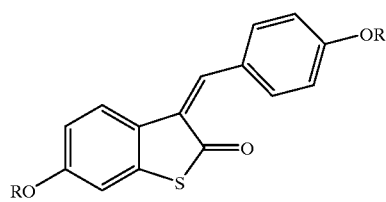

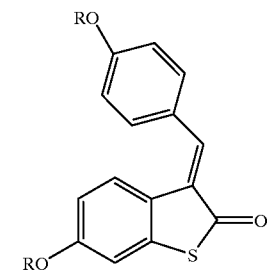

Both isomers are included in the scope of the claimed compounds.

The compounds of formula V and IX each contain two chiral centers, as illustrated below, and are thus diastereomeric and enantiomeric:

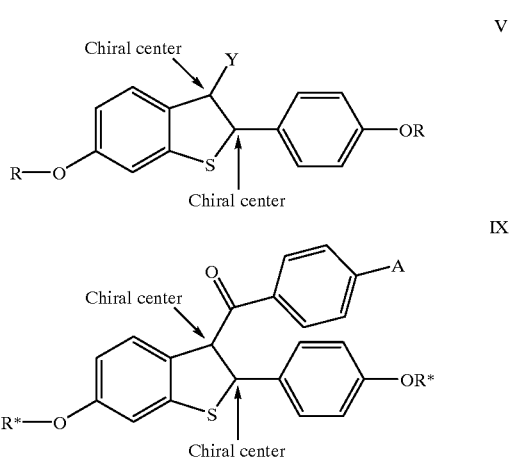

Thus, compounds of formula V and X include both diastereomers, as well as both enantiomers of each diastereomer, and mixtures thereof.

The overall process of the present invention is depicted hereinbelow in Schemes 1–3.

Compounds of formula IV may be prepared as shown in Scheme 1. Starting compounds of formula I may be prepared as taught in U.S. Pat. No. 4,443,451, the disclosure of which is herein incorporated by reference, by the conversion to the corresponding thianaphthen-2-one of formula II via treatment with a suitable acid. A hydrogen α to the carbonyl of the thianaphthen-2-one is removed with a suitable base, and the corresponding anion of a compound of formula II may be condensed with an appropriately substituted commercially available benzaldehyde of formula III to give the compounds of formula IV. This chemistry is illustrated in Scheme 1, wherein R is as described, supra.

Scheme 1

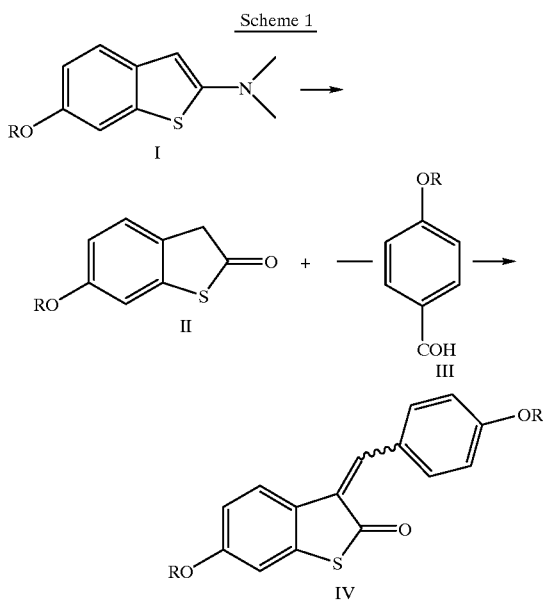

Compounds of formula II may be prepared from compounds of formula I. For example, a compound of formula I, dissolved in a suitable solvent, may be treated with a suitable acid to provide a compound of formula II. Suitable solvents include chloroform, methylene chloride, lower alcohols, toluene, acetonitrile, dimethylformamide, dimethylsulfoxide, ethyl acetate, mixtures thereof, and the like. A mixture of water and tetrahydrofuran is the preferred solvent. Suitable acids include inorganic acids, such as hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid, and the like. Hydrochloric acid is typically the preferred acid. The reaction is typically and preferably run at the reflux temperature of the solvent for about 3 hours.

A compound of formula IV may be prepared from a compound of formula II. For example, compounds of formula II may be dissolved in a suitable solvent, followed by the addition of a compound of formula III and a suitable base. Suitable solvents include chloroform, methylene chloride, lower alcohols, toluene, acetonitrile, dimethylformamide, dimethylsulfoxide, ethyl acetate, mixtures thereof, and the like. A mixture of tetrahydrofuran and ethanol is the preferred solvent. Suitable bases include ammonium or alkali or alkaline earth metal hydroxides, carbonates, bicarbonates, and the like, tri($C_1$-$C_4$) alkylamines, and the like, or 4-dimethylaminopyridine. Piperidine is the preferred base. The compound of formula III is generally employed in a slight molar excess. For example, a 1.01 to 1.1 molar excess, relative to the compound of formula II, is generally employed. A 1.02 molar excess is preferred. The base is generally employed in a catalytic fashion. For example, a 5 to 20 molar percent, relative to the compound of formula II, is generally employed. A 10 molar percent is preferred. The reaction is preferably carried out at about 5° C. for about 16 hours.

Compounds of formula V where Y is —$CO_2R^1$ and $R^1$ is not hydrogen may be prepared from compounds of formula IV. For example, a compound of formula IV may be treated with a lower alcohol in the presence of a suitable base. A compound of formula V where Y is —CO-halo may be prepared from a compound of formula Va by cleavage of the alkyl ester with a suitable base and treating the resulting compound of formula V where Y is —$CO_2H$ with a suitable halogenating reagent. A compound of formula V where Y is —CON(Me)(OMe) may be prepared from a compound of formula Vc by treatment with a compound of the formula HN(Me)(OMe) and a suitable base. A compound of formula V wherein Y is cyano may be prepared from a compound of formula Vb by treatment with ammonia followed by reaction with an suitable base and trifluoroacetic acid anhydride. This chemistry is illustrated in Scheme 2 hereinbelow, where $R^4$ is $C_1$-$C_4$ alkyl and R is as described, supra:

Scheme 2

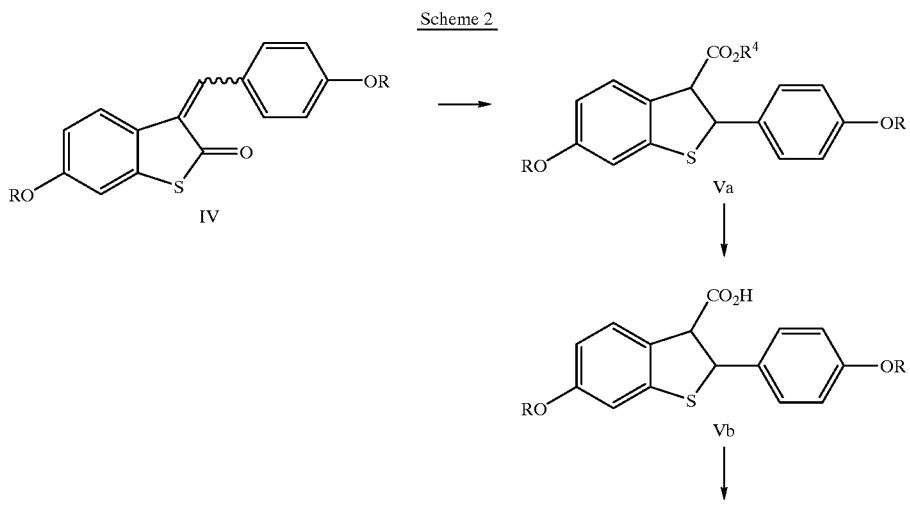

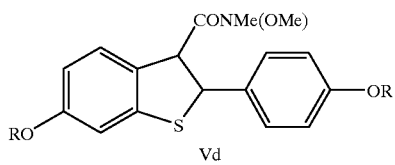

Vd

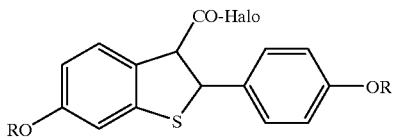

Vc

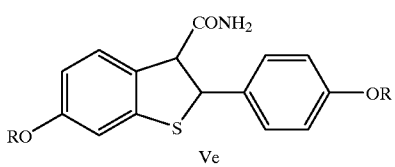

Ve

Vf

A compound of formula Va may be prepared from a compound of formula IV. For example, a compound of formula IV may be dissolved in a lower alcohol followed by the addition of a suitable base. The lower alcohol is preferably methanol. Suitable bases include ammonium or alkali or alkaline earth metal hydroxides, carbonates, bicarbonates, and the like, tri($C_1$-$C_4$)alkylamines (for example, triethylamine) and the like, or 4-dimethylaminopyridine. Piperidine is the preferred base. The reaction is preferably carried out at about the reflux temperature of the solvent employed for about 3 hours.

Compounds of formula Vb may be prepared from compounds of formula Va. For example, a compound of formula Va may be dissolved in a suitable solvent and a suitable base added. Suitable solvents include chloroform, tetrahydrofuran, methylene chloride, lower alcohols, toluene, acetonitrile, dimethylformamide, dimethylsulfoxide, ethyl acetate, mixtures thereof, and the like. A mixture of methanol and water is typically the preferred solvent. Suitable bases include ammonium or alkali or alkaline earth metal hydroxides, carbonates, bicarbonates, and the like, tri($C_1$-$C_4$)alkylamines and the like, or 4-dimethylaminopyridine. Potassium hydroxide is the preferred base. The reaction is preferably carried out at about the reflux temperature of the solvent employed for about 16 hours.

Compounds of formula Vc may be prepared from compounds of formula Vb. For example, a compound of formula Vb may be dissolved in a suitable solvent before a halogenating reagent is added. Suitable solvents include chloroform, tetrahydrofuran, toluene, acetonitrile, dimethylformamide, dimethylsulfoxide, ethyl acetate, mixtures thereof, and the like. Methylene chloride is typically the preferred solvent. Suitable halogenating reagents include, but are not limited to, benzeneseleninylchloride/aluminum chloride, thionyl bromide, N-bromo-succinimide, N-iodo-succinimide, and the like. Chlorine is the preferred halo group, and thionyl chloride is the preferred chlorinating reagent. The halogenating reagent is generally employed in a substantial molar excess. For example, a 1.5 to 3 molar excess, relative to the carboxylic acid intermediate, is generally employed. A 2.3 molar excess is preferred. The reaction is preferably carried out at about the reflux temperature of the solvent for about 2 hours in the presence of a catalytic amount of dimethylformamide.

A compound of formula Vd may be prepared from a compound of formula Vc. For example, N,O-dimethylhydroxylamine hydrochloride may be dissolved in a suitable solvent and a suitable base, followed by a compound of formula Vc, which is added to form the Weinreb amide. Suitable solvents include chloroform, tetrahydrofuran, lower alcohols, toluene, acetonitrile, dimethylformamide, dimethylsulfoxide, ethyl acetate, mixtures thereof, and the like. Methylene chloride is the preferred solvent. Suitable bases include ammonium or alkali or alkaline earth metal hydroxides, carbonates, bicarbonates, and the like, tri($C_1$-$C_4$)alkylamines, and the like, or 4-dimethylaminopyridine, and the like. Pyridine is the preferred base. The N,O-dimethylhydroxylamine hydrochloride is generally employed in a slight molar excess. For example, a 1.1 to 1.3 molar excess, relative to the compound of formula Vc, is generally employed. A 1.15 molar excess is preferred. The base is generally employed in a substantial molar excess. For example, a 2 to 3 molar excess, relative to the compound of formula Vc, is generally employed. A 2.5 molar excess is preferred. The reaction is typically carried out at about 5° C. when combining the reactants and then at about room temperature for about 16 hours.

A compound of formula Vg may be prepared from a compound of formula Vc. For example, a compound of formula Vc dissolved in a suitable solvent may be added to a solution of ammonia to form the carboxamide intermediate of formula Ve. Suitable solvents include chloroform, toluene, acetonitrile, dimethylformamide, dimethylsulfoxide, ethyl acetate, mixtures thereof, and the like. A mixture of methylene chloride and tetrahydrofuran is typically the preferred solvent. The reaction is preferably performed at -78° C. for 1 hour, followed by room temperature for 16 hours. This crude intermediate is then dissolved in a suitable solvent and a suitable base and trifluoroacetic acid anhydride added to provide the compounds of formula Vf. Suitable solvents include chloroform, methylene chloride, toluene, acetonitrile, dimethylformamide, dimethylsulfoxide, ethyl acetate, mixtures thereof, and the like. Tetrahydrofuran is the preferred solvent. Suitable bases include ammonium or alkali or alkaline earth metal hydroxides, carbonates, bicarbonates, and the like, tri($C_1$-$C_4$)alkylamines, and the like, or 4-dimethylaminopyridine. Triethylamine is the preferred base. The base is generally employed in a substantial molar excess. For example, a 2 to 3 molar excess, relative to the compound of formula Vc, is generally employed. A 2.5 molar excess is preferred. The trifluoroacetic anhydride is generally employed in a slight molar excess. For example, a 1 to 1.5 molar excess, relative to the compound of formula Vc, is generally employed. A 1.25 molar excess is preferred. The reaction is typically and preferably carried out at about 5° C. when combining the reactants, followed by room temperature for about 16 hours.

A compound of formula X may be prepared from a compound of formula Vg. For example, a compound of formula VI may be acylated with a compound of formula Vh and the resulting product oxidized with a suitable oxidizing reagent. The hydroxy protecting groups may optionally be removed by treatment with a suitable Lewis acid to provide a compound of formula X. This chemistry is illustrated in Scheme 3 where $R^*$ is independently at each occurrence a hydroxy protecting group or hydrogen, $Y^1$ is —$CO_2R^1$, —CO-halo, —CONMe(OMe), or cyano, and A and R are as described, supra.

When $Y^1$ is not cyano, the preferred X group of the compounds of formula VI is —MgBr. When $Y^1$ is cyano, the preferred X group is lithium. Preferred compounds of formula VI and VII are those where A is —O—$(CH_2)_2$—$NR^2R^3$. Especially preferred compounds of formula VI and VII are those where A is —$(CH_2)_2$—$NR^2R^3$, and $R^2$ and $R^3$ combine to form, together with the nitrogen atom to which they are attached, a piperidinyl ring.

OXIDATION

A compound of formula VIII may be prepared from a compound of formula VII. For example, a compound

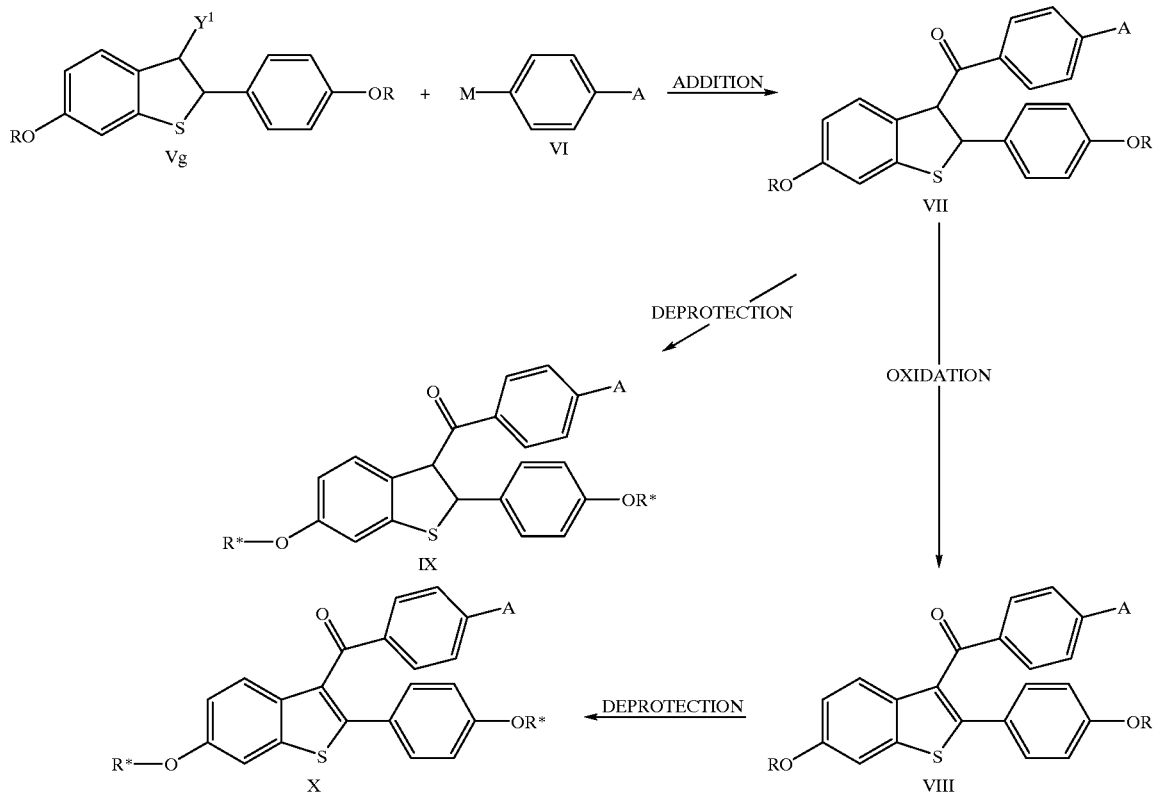

Scheme 3

ADDITION

A compound of formula VII may be prepared from a compound of formula Vg and VI. For example, a compound of formula Vg may be dissolved in a suitable solvent, followed by the addition of a compound of formula VI. Suitable solvents include chloroform, methylene chloride, $C_1$-$C_4$ ethers such as diethyl ether, and the like, alkanes such as hexane, heptane, cyclohexane, and the like, dimethylformamide, dimethylsulfoxide, mixtures thereof, and the like. Tetrahydrofuran is the preferred solvent. The compound of formula VI is employed in varying amounts depending on the particular $Y^1$ group. For example, when $Y^1$ is —$CO_2R^1$, a 5.1 molar excess, relative to the compound of formula Vh, is employed. When $Y^1$ is —CO-halo or —CONMe(OMe), a 1.2 to 1.5 molar excess is employed. When $Y^1$ is cyano, an equimolar amount is employed.

In general, when the hydroxy protecting groups contain a carbonyl, for example, when they are ester protecting groups, the preferred method of addition is by a Friedel Crafts acylation (for example, where M is hydrogen and Y is —CO-halo in the presence of a Lewis Acid catalyst).

of-formula VII may be dissolved in a suitable solvent, and an oxidizing reagent added. Suitable solvents include chloroform, methylene chloride, lower alcohols, acetonitrile, dimethylformamide, dimethylsulfoxide, ethyl acetate, mixtures thereof, and the like. Toluene is the preferred solvent. Suitable oxidizing reagents include triphenylmethylperchlorate. 2,3-Dichloro-5,6-dicyano-1,4-benzoquinone or oxygen gas/lithium tert-butoxide are the preferred oxidizing reagents. The oxidizing reagent is generally employed in a slight molar excess. For example, a 1.01 to 1.1 molar excess, relative to the compound of formula VII, is generally employed. A 1.02 molar excess is preferred. The reaction is preferably carried out at about the reflux temperature of the solvent for about 16 hours.

DEPROTECTION

In general, methods for protecting hydroxy groups with one of the groups listed above, or in Greene, and for cleaving or removing the protecting groups to afford compounds of formula X, where $R^*$ is hydrogen, may be found in Greene and are thus well known to one skilled in the art.

More specifically, compounds of formula X where R* is hydrogen may be prepared from compounds of formula VIII. For example, a compound of formula VIII where R is $C_1$-$C_4$ alkyl, may be dissolved in a suitable solvent, and a Lewis acid added. Suitable solvents include chloroform, methylene chloride, 1,2 dichloroethane, chlorobenzene, carbon tetrachloride, mixtures thereof, and the like. Methylene chloride is the preferred solvent. Boron trichloride is the preferred Lewis acid. The Lewis acid is generally employed in a substantial molar excess. For example, a 2 to 4 molar excess, relative to the compound of formula VIII, is generally employed. A 3 molar excess is preferred. The reaction is typically and preferably carried out at about 35° C. for about 4 to 48 hours.

In addition, compounds of formula VIII where R* is methyl may be deprotected by the use of thiol reagents as taught in U.S. Pat. No. 4,380,635, the disclosure of which is herein incorporated by reference. A compound of formula VIII where R* is —CO—($C_1$-$C_6$ alkyl) or —CO—Ar may be deprotected by the methods taught in U.S. Pat. No. 4,358,593, the disclosure of which is herein incorporated by reference.

The skilled artisan will recognize that to access the compounds of formula IX, where R* is not hydrogen, only the ADDITION step need be performed. To access the compounds of formula IX where R* is hydrogen both the ADDITION and DEPROTECTION steps must be performed. Similarly, to access the compounds of formula X, where R* is not hydrogen, only the ADDITION and OXIDATION steps need be performed. To access the compounds of formula X where R* is hydrogen, the ADDITION, OXIDATION, and DEPROTECTION steps must be performed. The skilled artisan will further appreciate that if a particular hydroxy protecting group is desired in a compound of formula IX or X, but that hydroxy protecting group is incompatible to a particular choice of reaction pathways of the invention, the desired hydroxy protecting group can be reattached as a last step in the synthesis according to well known methods in the art, for example, those described in Greene.

The skilled artisan will appreciate that the order in which the steps are performed in Scheme 3 is not important in many cases. For example, the order of the ADDITION and OXIDATION steps may be reversed. Additionally, the steps of ADDITION and DEPROTECTION may be performed before OXIDATION. Furthermore, the manipulations of the Y group described in Scheme 2 can be performed after OXIDATION as described in Scheme 3. These variations demonstrated in the following Preparations and Examples.

Compounds of formula IX or X where A is not —O—$(CH_2)_2$—$NR^2R^3$ may be converted to compounds of formula IX or X where A is —O—$(CH_2)_2$—$NR^2R^3$. For example, the alkoxide of an alcohol of the formula HO—$(CH_2)_2$—$NR^2R^3$ (preferably the sodium alkoxide generated from mixing the alcohol with sodium hydride) in a polar aprotic solvent (for example, tetrahydrofuran, dimethylsulfoxide, or dimethylformamide) may be reacted with a compound of formula IX or X where A is halo or nitro. Dimethylformamide is the preferred solvent.

Compounds of formula IX or X where A is hydroxy may be converted to compounds of formula IX or X where A is —O—$(CH_2)_2$—$NR^2R^3$ by dissolving a compound of formula IX or X in a suitable solvent, in the presence of a suitable base, and adding a compound of the formula Z—$(CH_2)_2$—$NR^2R^3$ where Z is halo or p-toluenesulfonyl. Suitable solvents include dimethylformamide, tetrahydrofuran, 1,3-dimethyl-2-imidazolidinone, mixtures thereof, and the like. Dimethylsulfoxide is the preferred solvent. Suitable bases include, non-kinetic bases such as carbonates, bicarbonates, or hydroxides, (for example, sodium hydroxide, potassium bicarbonate, or sodium hydroxide) and kinetic bases such as alkyl lithiums (for example, n-butyl lithium) or sodium hydride. A kinetic base, specifically sodium hydride, is the preferred base. The base is typically employed in a slight molar excess. For example, a 1.01 to 1.15 molar excess, relative to the starting compound of IX or X is generally employed. A 1.05 molar excess is preferred. The compound of formula Z—$(CH_2)_2$—$NR^2R^3$ is typically employed in a slight molar excess. For example, a 1.01 to 1.15 molar excess, relative to the starting compound of formula IX or X, is generally employed. A 1.05 molar excess is typically preferred. The reaction is preferably carried out at about 35° C. for about 2 hours after addition of the base and then at about 65° C. for about 16 hours after the addition of the compound of formula Z—$(CH_2)_2$—$NR^2R^3$.

Compounds of formula IX and X where A is $C_1$-$C_4$ alkoxy may be converted to compounds of formula IX or X where A is —O—$(CH_2)_2$—$NR^2R^3$ by first removing the $C_1$-$C_4$ alkyl group as described in the DEPROTECTION section hereinabove to give the compound of formula IX and X where A is hydroxy, and then converting the resulting compound by the method in the previous paragraph. Compounds of formula IX or X where A is —O—$(CH_2)_2$-halo may be converted to compounds of formula IX or X where A is —O—$(CH_2)_2$—$NR^2R^3$ by the methods taught in U.S. Pat. No. 4,358,593.

In general, the transformations of Schemes 1–3 are substantially complete in about 15 minutes to 72 hours when conducted at a temperature range of from about −78° C. to the reflux temperature of the reaction mixture. Solvent choice is not critical so long as the solvent employed is inert to the ongoing reaction and the reactants are sufficiently solubilized to effect the desired reaction. Once a reaction is complete, the intermediate compound may be isolated, if desired, by procedures known in the art. For example, the compound may be crystallized and then collected by filtration, or the reaction solvent may be removed by extraction, evaporation, or decantation. The intermediate may be further purified, if desired, by common techniques such as recrystallization or chromatography over solid supports such as silica gel or alumina. The compounds of formula II–VIII, Va–Vd, and Vf are preferably isolated and purified before use in subsequent reactions.

The following Preparations and Examples further illustrate specific aspects of the present invention. It is to be understood, however, that these examples are included for illustrative purposes only and are not intended to limit the scope of the invention in any respect and should not be so construed.

EXAMPLES

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS(FD)", "MS(FAB)", "IR", "UV", "Analysis", "HPLC", and "TLC", respectively. The values reported for MS(FD) correspond to mass numbers unless otherwise indicated. In addition, the absorption maxima listed for the IR spectra are only those of interest and not all of the maxima observed.

PREPARATION 1

1-Magnesiumbromo-4-(1-Piperidinyl)ethoxybenzene

Step 1

Preparation of 4-bromo-(1-piperidinyl)ethoxybenzene

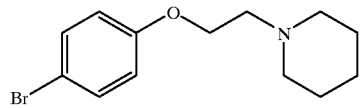

To bromophenol (20.05 g, 116 mmol) and finely powdered potassium carbonate (49.16 g, 356 mmol) is added 250 ml of dimethylformamide and the contents heated with vigorous stirring to 90° C. To this rapidly stirring slurry is added β-chloroethyl piperidine hydrochloride salt (25.6 g, 139 mmol) in portions over 5 minutes. The resulting slurry is heated at 90° C. and stirred for 2 hours. An aliquot at that time shows the reaction about 95% complete. Additional potassium carbonate (4.2 g) and β-chloroethyl piperidine hydrochloride salt (2.33 g) is added to drive the reaction to completion. The reaction is heated for 2 more hours, then cooled and stirred at room temperature overnight. $^1$H NMR shows the reaction complete therefore the solids are filtered and the filtrate partitioned between water (200 ml) and diethyl ether (200 ml). The ether layer is washed with water (3×200 ml), brine, and 1N hydrochloric acid (2×50 ml). The combined extracts are made basic with 25 ml of 5N sodium hydroxide and extracted with diethyl ether (2×150 ml). The organics are dried over magnesium sulfate, filtered, and concentrated to give 27.2 g of an orange oil which is used as is without further purification. (73%).

Step 2

Preparation of 1-Magnesiumbromo-4-(lPiperidinyl)ethoxybenzene

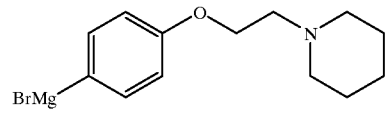

To 30 ml of dry tetrahydrofuran containing mortar and pestle ground magnesium (802 mg) under nitrogen is added 2 ml of 4-bromo-(1-piperidinyl)ethoxybenzene. No exotherm observed, so external heat is applied and a small crystal of iodine is added. As the temperature rises, the reaction is initiated. More 4-bromo-(1-piperidinyl)ethoxybenzene (total is 9.97 g, 31.1 mmol) is then added via syringe pump at a rate to maintain the reaction (about 30 minutes). Following the completion of the addition, the reaction is heated at reflux for 1 hour. At that time, the magnesium is essentially gone except for a trace. The cooled solution is transferred via cannula to an oven dried flask under nitrogen to afford a red solution. The solution is triturated by taking 1–2 mgs of 9,19-phenanthroline in 4 ml of tetrahydrofuran and adding 1.00 ml of a Grignard solution. A purple/brown color formed after about 30 seconds. This solution is triturated with isopropanol (58 ml). 58 ml×0.785 mg/ml×1 mmol/60.1 mg=0.785 M. (95.7%).

PREPARATION 2

6-Methoxythianaphthen-2-one

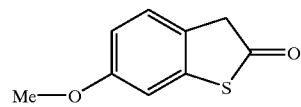

To tetrahydrofuran (200 ml) containing 2-dimethylamino-6-methoxybenzo[b] thiophene (20.00 g, 96.5 mmol) is added 1N aqueous hydrochloric acid (200 ml) and the resulting mixture is heated to reflux for 3 hours. The mixture is cooled, the layers are separated, and the aqueous layer is extracted with methylene chloride (300 ml). The combined organic layers washed with water (250 ml), dried over magnesium sulfate, filtered and concentrated to give crude product, which is recrystallized from ethanol, and dried in vacuo at room temperature to afford the title compound (13.89 g, 77.0 mmol, 80%): mp 80–82° C.; IR (KBr) 1713, 1605, 1485, 1287, 1015, 865, 813 cm$^{-1}$; $^1$H NMR (DMSO-d$_6$) δ7.22 (d, 1 H, J=8.4 Hz), 7.11 (s, 1 H), 6.78 (d, 1 H, J=8.4 Hz), 4.06 (s, 2 H), 3.71 (s, 3 H); $^{13}$C NMR (DMSO-d$_6$) d 203.5, 159.0, 136.9, 125.6, 124.6, 112.3, 108.4, 55.3, 46.2. Anal. Calcd. for C$_9$H$_8$O$_2$S: C, 59.98; H, 4.47; S, 17.78. Found: C, 60.19; H, 4.57; S, 18.03.

EXAMPLE 1

6-Methoxy-3-[(4-Methoxyphenyl)methylene]benzo[b]thiophene-2(3H)

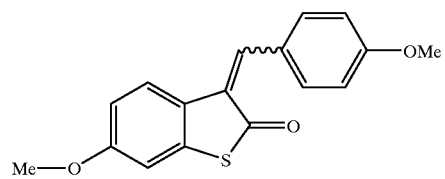

To 6-methoxythianaphthen-2-one (3.99 g, 22.13 mmol), ethanol (25 ml) and tetrahydrofuran (12.5 ml) at 5° C. is added p-anisaldehyde (2.75 ml, 3.08 g, 22.6 mmol), and piperidine (0.2 ml). The resulting mixture is stirred at 5° C. for 16 hours. The volatile components are removed in vacuo, and the crude solid product is recrystallized from ethanol (25 ml) to afford material as a mixture of E- and Zisomers (3.00 g, 45%): mp 103.1–104.5° C.; IR (KBr) 1683, 1591, 1513, 1465, 1261, 1240, 1046, 1023 cm$^{-1}$; $^1$H NMR (CDCl$_3$) δ8.02 (d, J=8.7 Hz), 7.69 (d, J=9.0 Hz), 7.56–7.53 (m), 7.42 (d, J=8.7 Hz), 7.31 (s), 6.95–6.82 (m), 6.76 (dd, J=8.7, 2.1 Hz), 6.56 (dd, J=8.7, 2.1 Hz), 3.86 (s, 3 H), 3.73 (s), 3.70 (s); $^{13}$C NMR (CDCl$_3$) d 195.1, 162.0, 160.9, 160.6, 160.3, 137.5, 136.8, 135.8, 134.3, 131.8, 131.2, 128.9, 126.7, 125.0, 123.4, 121.8, 114.3, 113.7, 112.5, 111.8, 108.6, 108.1, 55.6, 55.5. Anal. Calcd. for C$_{17}$H$_{14}$O$_3$S: C, 68.44; H, 4.73; S, 10.75. Found: C, 68.25; H, 4.68; S, 10.97.

EXAMPLE 2

2-(4-Methoxyphenyl)-3-(4-(2-Piperidinoethoxy)benzoyl)-6-Hydroxybenzo[b]thiophene

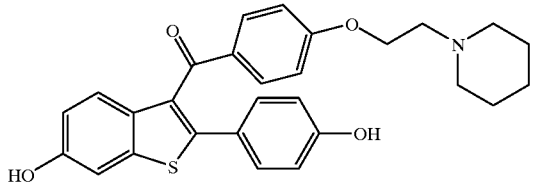

Step 1

Preparation of 2,3-Dihydro-6-Methoxy-2-(4-Methoxyphenyl)benzo[b]thiophene-3-Carboxylic Acid Methyl Ester

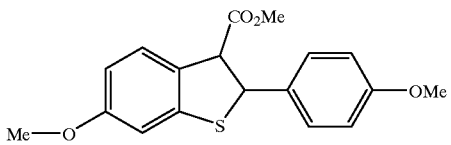

A slurry of 6-methoxy-3-[(4-methoxyphenyl)methylene]-benzo[b]thiophene-2 (3H) (2.00 g, 6.7 mmol) in methanol (20 ml) is treated with piperidine (0.75 ml) and the contents heated to reflux for 3 hours. The resulting solution is cooled and concentrated, and the crude solid product is recrystallized from methanol (15 ml), and dried in vacuo to afford 1.58 g (4.78 mmol, 71%) of title compound: mp 98.3–99.8° C.; IR (KBr) 1737, 1596, 1516, 1488, 1271, 1216, 1020 cm$^{-1}$; $^1$H NMR (CDCl$_3$): δ7.36 (d, 2 H, J=8.4 Hz), 7.13 (d, 1 H, J=8.7 Hz), 6.83 (d, 2 H, J=8.7 Hz), 6.75 (d, 1 H, J=2.4 Hz), 6.62 (dd, 1 H, J=8.4, 2.4 Hz), 5.41 (d, 1 H, J=8.1 Hz), 4.37 (d, 1 H, J=8.1 Hz), 3.78 (s, 6 H), 3.75 (s, 3 H); $^{13}$C NMR (CDCl$_3$): d 171.8, 160.5, 159.5, 142.8, 132.2, 128.8, 128.2, 125.6, 114.2, 110.9, 107.4, 60.5, 55.6, 55.5, 55.4, 52.6. Anal. Calcd. for C$_{18}$H$_{18}$O$_4$S: C, 65.44; H, 5.49; S, 9.70. Found: C, 65.39; H, 5.35; S, 9.97.

Step 2

Preparation of 2,3-Dihydro-6-Methoxy-2-(4-Methoxyphenyl)benzo[b]thiophene-3-Carboxylic Acid

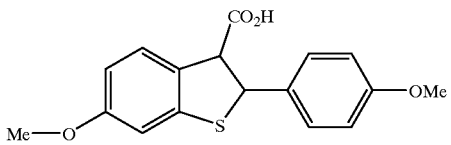

To a solution of 2,3-dihydro-6-methoxy-2-(4-methoxyphenyl)benzo[b]thiophene-3-carboxylic acid methyl ester (0.7337 g, 2.21 mmol) in methanol (10 ml) at 5° C. was added 5 N sodium hydroxide (1 ml, 5 mmol) and water (5 ml). The resulting slurry was stirred at that temperature for 1 hour, then toluene (5 ml) was added, and the resulting mixture was stirred at room temperature for 16 hours. Additional 5 N sodium hydroxide (1 ml) was then added, and the mixture stirred an additional 16 hours. The reaction mixture was then diluted with water (5 ml) and diethyl ether (20 ml), and the layers separated. The aqueous layer was acidified to pH 1 with 1 N hydrochloric acid, and extracted with diethyl ether (2×50 ml). The ether layers were combined, dried (magnesium sulfate), filtered and concentrated to a foam, which was further dried in vacuo to afford 0.6146 g (88%) of title compound. IR (KBr) 3300-2800 (br), 2836, 1710, 1611, 1594, 1514, 1482, 1248, 1181, 1030 cm$^{-1}$; $^1$H NMR (CDCl$_3$): δ11.63 (br s, 1 H), 7.37 (d, 2 H, J=8.4 Hz); 7.24 (d, 1 H, J=8.4 Hz), 6.85 (d, 2 H, J=8.4 Hz), 6.78 (d, 1 H, J=2.2 Hz), 6.67 (dd, 1 H, J=8.4, 2.2 Hz), 5.38 (d, 1 H, J=7.5 Hz), 4.42 (d, 1 H, J=7.5 Hz), 3.79 (s, 6 H); $^{13}$C NMR (CDCl$_3$): d 177.7, 160.7, 159.5, 142.8, 132.3, 128.7, 127.3, 126.0, 114.3, 111.0, 107.5, 60.3, 55.6, 55.4, 55.1. Anal. calcd. for C$_{17}$H$_{16}$O$_4$S: C, 64.54; H, 5.10; S; 10.13. Found: C, 64.78; H, 5.14; S, 10.55.

Step 3

Preparation of 2,3-Dihydro-6-Methoxy-2-(4-Methoxyphenyl)-N-Methoxy-N-Methylbenzo[b]thiophene-3-Carboxamide

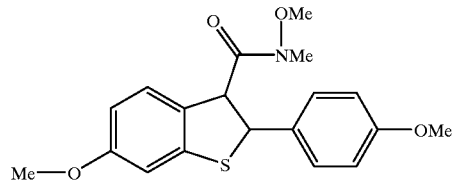

To a mixture of 2,3-dihydro-6-methoxy-2-(4-methoxyphenyl)benzo[b]thiophene-3-carboxylic acid (349.4 mg, 1.105 mmol) and methylene chloride (4 ml) is added thionyl chloride (195.7 mg, 1.645 mmol) and a catalytic amount of N, N-dimethylformamide. The contents are heated to reflux for 1 hour, then cooled and concentrated to a residue. This is then subjected to three cycles of dissolution in toluene and reconcentration, and the resulting residue taken up in methylene chloride (4 ml). To this solution is added N, O-dimethylhydroxylamine hydrochloride (118.9 mg, 1.22 mmol) and the resulting suspension cooled to 5° C. Pyridine (215 mg, 2.71 mmol) is then added via syringe. The reaction is allowed to warm to room temperature and is stirred for 16 hours. The contents are then partitioned between methylene chloride and water, and the layers separated. The organic layer is washed sequentially with 1 N hydrochloric acid, saturated aqueous sodium bicarbonate, and water, then dried over magnesium sulfate, filtered and concentrated to an oil. The oil is then chromatographed on silica gel (6:4 hexanes:ethylacetate) to afford 262.5 mg (66.1%) of title compound. IR (KBr) 2960, 2905, 1660, 1511, 1479, 1246, 1178, 1059 cm$^{-1}$; $^1$H NMR (CDCl$_3$): δ7.46 (d, 2 H, J=8.1 Hz), 6.85 (m, 3 H), 6.74 (s, 1 H), 6.57 (d, 1 H, J=8.1 Hz), 5.54 (d, 1 H, J=10.5 Hz), 4.82 (d, 1 H, J=10.5), 3.77 (s, 3 H), 3.75 (s, 3 H), 3.42 (s, 3 H), 3.23 (s, 3 H); $^{13}$C NMR (CDCl$_3$): d 172.0, 160.2, 159.5, 143.1, 131.1, 130.2, 129.2, 124.9, 114.1, 110.9, 107.6, 61.7, 57.8, 57.3, 55.5, 55.3, 32.6. Anal. Calcd. for C$_{19}$H$_{21}$NO$_4$S: C, 63.49; H, 5.89, N, 3.90; S, 8.92. Found: C, 63.48; H, 5.90; N, 3.81; S, 8.64.

Step 4

Preparation of 2,3-Dihydro-[6-Methoxy-3-(4-methoxyphenyl)benzo[b]thien-3-yl][4-(2-{1-Piperidinyl}ethoxy)phenyl]methananone

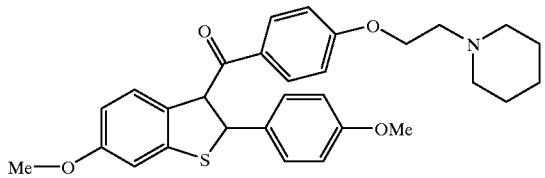

The 2,3-dihydro-6-methoxy -2-(4-methoxyphenyl)-N-methoxy-N-methylbenzo[b]thiophene-3-carboxamide (108 mg, 0.300 mmol) is dissolved in dry tetrahydrofuran (3 ml) under a nitrogen atmosphere to give a clear colorless solution. The addition of 1-magnesiumbromo-4-(1-piperidinyl)ethoxybenzene (0.74 M in tetrahydrofuran, 1.22 ml, 0.90 mmol) via syringe as one portion produced a yellow orange solution with minimal exotherm. After stirring for about 60 hours, the mixture is combined with methylene chloride (5 ml) and hydrochloric acid (1 N, 3 ml). The resulting layers are separated, and the top aqueous phase is re-extracted with methylene chloride (3 ml). The combined organic layers are concentrated in vacuo to give a yellow foam (0.26 g). This crude product is purified by flash silica gel chromatography with 5:1:1 heptane:methylene chloride:triethylamine as the eluent, and then crystallized from methylene chloride/heptane to yield, after drying in vacuo at 50° C., 120 mg of the title compound. (79.5%). mp 130–132°; MS(FD) 503, Anal.Calcd. for $C_{30}H_{33}NO_4S$: C, 71.54;H,6.60;N,2.78;S, 6.37. Found C,71,33;H,6.71,N,2.72;S,6.32.

Step 5

Preparation of [6-Methoxy-2-(4-Methoxyphenyl)benzo[b]thien-3-yl]-[4-[2-(1-Piperidinyl)ethoxy]phenyl] Methanone

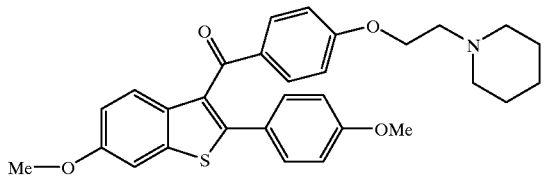

The 2,3-dihydro-[6-methoxy-3-(4-methoxyphenyl)benzo[b]thien-3-yl][4-(2-{1-piperidinyl}ethoxy)phenyl]methananone (500 mg, 1.00 mmol) is combined with dimethylsulfoxide (5 ml) and a 1 M solution of potassium tert-butoxide in tert-butanol (2 ml, 2 mmol). Oxygen is then bubbled in subsurface until all of the starting material had reacted (about 2.5 hours) as determined by HPLC (25 cm Zorbax RX-C8; 7:3 acetonitrile: 0.05 M potassium dihydrogen phosphate/phosphoric acid to pH 2.5; 1.5 ml/min; 280 nm). The addition of methylene chloride (25 ml) and aqueous ammonium chloride solution (35 ml) produced two separable layers. The organic phase is concentrated in vacuo to 0.61 g of greenish-brown oil, which is purified via silica gel flash chromatography with an eluent of 100:5:0.5 methylene chloride:ethanol:ammonium hydroxide to give 40 mg of the title compound. (8.0%). $^1$H NMR.

Step 6

Preparation of 6-Hydroxy-2-(4-Hydroxyphenyl)-3-[4(2-Piperidinoethoxy)benzoyl]benzo[b]thiophene Boron trichloride gas is condensed into a cold graduated cylinder (2.8 ml), and added to a solution of [6-methoxy-2-(4-methoxyphenyl)-benzo-[b]-thien-3-yl] [4-[2-(1-piperidinyl)ethoxy]phenyl] methanone (6.37 g, 12.7 mmol) in 52 ml of 1,2-dichloroethane. The resulting solution is heated to 35° C. After about 16 hours the reaction is complete. Methanol (30 ml) is added to the reaction mixture over a 20 minute period, causing the methanol to reflux. The resulting slurry was stirred at 25° C. After 1 hour, the crystalline product is filtered, washed with cold methanol (8 ml), and dried at 40 ° C. in vacuo to give 5.14 g of the title compound. mp 225° C.

EXAMPLE 3

2-(4-Methoxyphenyl)-3-(4-(2-Piperidinoethoxy)benzoyl)-6-Hydroxybenzo[b]thiophene

Step 1

Preparation of 2,3-Dihydro-[6-Hydroxy-3-(4-Hydroxyphenyl)benzo[b]thien-3-yl][4-(2-{1-Piperidinyl}ethoxy)phenyl]methanone

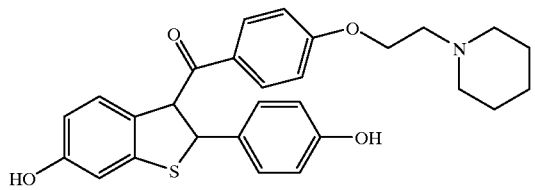

A solution of 2,3-dihydro-[6-methoxy-3-(4-methoxyphenyl)benzo[b]thien-3-yl][4-(2-{1-piperidinyl}ethoxy)phenyl]methananone (520 mg, 1.03 mmol) in methylene chloride (7 ml) is converted to its hydrochloride salt by bubbling hydrogen chloride gas subsurface for 10 minutes. Using a water bath for cooling and under a nitrogen atmosphere, aluminum chloride powder (1.1 g, 8.26 mmol) is carefully added to the solution to produce a hazy red mixture. After 10 minutes, 1-propanethiol (0.28 ml, 0.24 g, 3.09 mmol) is added. After 2.5 hours the starting material had all reacted as determined by HPLC (25 cm Zorbax RX-C8; 7:3 acetonitrile: 0.05 M potassium dihydrogen phosphate/phosphoric acid to pH 2.5; 0.5 ml/min; 280 nm), so the mixture is quenched by the dropwise addition of tetrahydrofuran (10 ml)/ethanol (5 ml) followed by 20% hydrochloric acid (5 ml). The resulting layers are separated, followed by repeated extraction of the aqueous phase with 2:1 methylene chloride:ethanol. The combined organic layers are concentrated in vacuo to 740 mg of beige foam, which is then purified via flash silica gel chromatography with 1:1 acetone:ethanol as the eluent to give 520 mg of the title compound is obtained as a yellow foam. HRMS(FAB+) calcd. for $C_{28}H_{30}NO_4S$=476.1896; Found 476.1912. 1H NMR (CD$_3$OD): δ7.91 (d, 2H), 7.25 (d, 2H), 7.01 (d, 2H), 6.6 (m, 4 H), 6.35 (dd, 1H), 5.40 (s, 2H), 4.82 (large s, H$_2$O peak), 4.31 (t, 2H), 3.29 (t, 1H), 3.20 (broad t, 2H), 2.95 (broad s, 4 H), 1.64 (broad m, 4 H), 1.59 (broad d, 2H).

Step 2

Preparation of 6-Hydroxy-2-(4-Hydroxyphenyl)-3-[4(2-Piperidinoethoxy)benzoyl]benzo[b]thiophene The 2,3-dihydro-[6-hydroxy-3-(4-hydroxyphenyl)benzo[b]thien-3-yl][4-(2-{1-piperidinyl}ethoxy)phenyl] methanone, (50 mg, 0.105 mmol), dimethylsulfoxide, (5 ml), lithium tert-butoxide (42 mg, 0.525 mmol), and tert-butanol (2 ml) are combined to give an orange mixture. Oxygen is bubbled in subsurface for 3 hours, during which the appearance changed to an opaque brown mixture. The mixture is worked up into two readily separable layers via the addition of 20% aqueous ammonium chloride solution (25 ml) and methylene chloride (15 ml). The organic phase is dried with anhydrous sodium sulfate and then concentrated in vacuo to an amber "glass" (70 mg). $^1$H NMR in $CD_3OD$ shows a 5:1 mixture of title product to starting material. MS(FAB+)-474.4.

EXAMPLE 4

2-(4-Methoxyphenyl)-3-(4-(2-Piperidinoethoxy) benzoyl)-6-Hydroxybenzo[b]thiophene

Step 1

Preparation of 6-Methoxy-2-(4-Methoxyphenyl) benzo[b]thiophene-3-Carboxylic Acid Methyl Ester

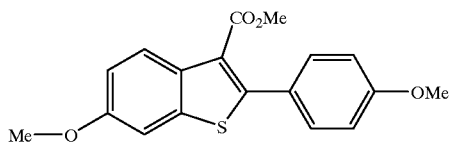

To toluene (20 ml) and 2,3-dihydro-6-methoxy-2-(4-methoxyphenyl)benzo[b]thiophene-3-carboxylic acid methyl ester (0.7365 g, 2.33 mmol) is added dichlorodicyanoquinone (0.5405 g, 2.38 mmol, 2.38 mmol). The mixture is placed under nitrogen and heated to reflux for 16 hours, then cooled and filtered. The filter cake is rinsed with additional toluene and the filtrate and rinse are combined and concentrated to afford crude product, which is purified by silica gel chromatography (9:1 hexanes:ethyl acetate) to afford 0.7178 g (98%) of title compound: mp 85.4–86.6° C.; IR (KBr) 3010, 2860, 1700, 1608, 1478, 1251, 1068, 1020 cm$^{-1}$; $^1$H NMR (CDCl$_3$): δ8.21 (d, 1 H, J=8.7 Hz), 7.44 (d, 2 H, J=8.4 Hz), 7.24 (s, 1 H), 7.07 (d, 1 H, J=9 Hz), 6.95 (d, 2 H, J=8.4 Hz), 3.87 (s, 3 H), 3.85 (s, 3 H), 3.78 (s, 3 H); $^{13}$C NMR (CDCl$_3$): d 164.6, 160.2, 157.7, 149.6, 139.8, 132.7, 130.9, 126.4, 125.4, 115.2, 113.7, 104.2, 55.7, 55.4, 51.6. Anal. Calcd. for $C_{18}H_{16}O_4S$: C, 65.84; H, 4.91; S, 9.76. Found: C, 65.72; H, 4.90; S, 10.04.

Step 2

Preparation of [6-Methoxy-2-(4-Methoxyphenyl) benzo[b]thien-3-yl]-[4-[2-(1-Piperidinyl)ethoxy] phenyl] Methanone To a solution of 6-methoxy-2-(4-methoxyphenyl)benzo [b]thiophene-3-carboxylic acid methyl ester (202 mg, 0.615 mmol) in tetrahydrofuran (5 ml) under nitrogen at 5° C. is added, dropwise over 2 min via syringe a solution of 4-[2-(1-piperidinyl)ethoxy]phenylmagnesium bromide (1.0 ml of 0.76 M solution, 0.76 mmol). Cooling is removed, and the reaction is allowed to stir at room temperature for 48 hours. It is then quenched by addition of saturated aqueous ammonium chloride (2 ml), and partitioned between methylene chloride and water. The organic phase is separated, dried over magnesium sulfate, filtered and concentrated to an oil, which is chromatographed on silica (5:1:1 hexanes:dichloromethane:triethylamine) to afford recovered starting material (46.0 mg, 23%) and title compound. The latter is further purified by dissolution in methylene chloride, followed by washing with 1 N hydrochloric acid, then 1 N sodium hydroxide. Drying over magnesium sulfate, filtration and concentration furnished 97.4 mg of title compound (0.194 mmol, 32%, 41% based on recovered starting material). IR (CHCl$_3$): 2932, 1647, 1597, 1475, 1252, 1163, 1029, 828 cm$^{-1}$; $^1$H NMR (CDCl$_3$) δ7.75 (d, 2H, J=8.7), 7.51 (d, 1H, J=8.7), 7.31 (m, 3H), 6.94 (dd, 1H, J=9.0, 2.4), 6.74 (m, 4 H), 4.07 (t, 2H, J=6.0), 3.87 (s, 3H), 3.73 (s, 3H), 2.72 (t, 2H, J=6.0), 2.47 (m, 4 H), 1.58 (m, 4 H), 1.42 (m, 2H); $^{13}$C NMR (CDCl$_3$) d 193.2, 163.1, 159.8, 157.7, 142.5, 140.1, 134.1, 132.4, 130.7, 130. 5, 130.3, 126.1, 124.1, 114.8, 114.3, 114.1, 104.6, 66.3, 57.8, 55.7, 55.3, 55.2, 26.0, 24.2. Anal. Calcd. for $C_{30}H_{31}NO_4S$: C, 71.83; H, 6.23; N, 2.79; S, 6.39. Found: C, 71.56; H, 6.27; N, 2.82; S, 6.26.

Step 3

Preparation of 6-Hydroxy-2-(4-Hydroxyphenyl)-3-[4(2-Piperidinoethoxy)benzoyl]benzo[b]thiophene The [6-Methoxy-2-(4-methoxyphenyl)-benzo[b]thien-3-yl] [4-[2-(1-piperidinyl)ethoxy]phenyl] methanone is converted to the title compound by the procedure of Example 2, step 6.

EXAMPLE 5

2-(4-Methoxyphenyl)-3-(4-(2-Piperidinoethoxy) benzoyl)-6-Hydroxybenzo[b]thiophene

Step 1

Preparation of 6-Methoxy -2-(4-Methoxyphenyl) benzo [b] thiophene-3-Carboxylic Acid

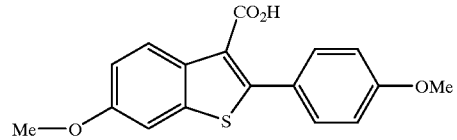

To methanol (25 ml) and water (10 ml) is added 2.5 N potassium hydroxide in methanol (7 ml, 18.5 mmol) and 6-methoxy-2-(4-methoxyphenyl)benzo[b]thiophene-3-carboxylic acid methyl ester (2.00 g, 6.09 mmol). The contents are heated to reflux for 16 hours, then cooled and poured into a solution of 1 N hydrochloric acid (50 ml). The resulting slurry is further diluted with water (75 ml), then filtered, and the filter cake rinsed with water, and dried in vacuo to afford 1.86 g (97%) of title compound. IR (KBr) 3100-2400 (br), 2935, 1673, 1608, 1527, 1433, 1250, 1178, 1030, 828 cm$^{-1}$; $^1$H NMR (CDCl$_3$/DMSO-d$_6$): δ8.27 (d, 1 H, J=9.0 Hz), 7.49 (d, 2 H, J=8.5 Hz), 7.26 (d, 1 H, J=1.7 Hz), 7.06 (dd, 1 H, J=9.0, 1.7 Hz), 6.93 (d, 2 H, J=8.5 Hz), 3.87 (s, 3 H), 3.84 (s, 3 H); $^{13}$C NMR (CDCl$_3$/DMSO-d$_6$): d 166.0, 160.1, 157.6, 148.5, 139.8, 133.2, 131.0, 126.6, 125.7, 123.0, 115.1, 113.8, 104.3, 55.7, 55.5. Anal. Calcd. for $C_{17}H_{14}O_4S$: C, 64.95; H, 4.49; S, 10.20. Found: C, 64.72; H, 4.49; S, 10.40.

Step 2

Preparation of 6-Methoxy-2-(4-Methoxyphenyl) benzo[b]thiophene-3-Carboxylic Acid Chloride

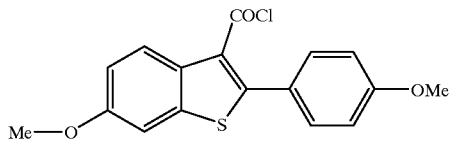

To a slurry of 6-methoxy -2-(4-methoxyphenyl)benzo[b] thiophene-3-carboxylic acid (0.0484 g, 0.154 mmol) in methylene chloride (5 ml) is added thionyl chloride (0.025 ml, 0.356 mmol), and a catalytic amount of N,N-dimethylformamide. The reaction is heated to reflux for 2 hours, then cooled and concentrated in vacuo. The residual material is dissolved in toluene (10 ml), and reconcentrated in vacuo. This dissolution/reconcentration procedure is repeated two more times to afford 0.0498 g (97%) of title compound as a solid: mp 135.5–137.9° C. IR (KBr) 2965, 1678, 1610, 1525, 1478, 1253, 815; $^1$H NMR (CDCl$_3$): δ8.13 (d, 1 H, J=9 Hz), 7.48 (d, 2 H, J=8.7 Hz), 7.27 (d, 1 H, J=2.4 Hz), 7.13 (dd, 1 H, J=9.0, 2.4 Hz), 7.00 (d, 2 H, J=8.7 Hz); $^{13}$C NMR (CDCl$_3$): d 163.4, 161.0, 158.2, 139.1, 131.3, 131.2, 129.1, 128.3, 125.1, 124.6, 115.9, 114.2, 104.4, 55.7, 55.5; Exact mass calcd. for $C_{18}H_{16}O_4S$ (in situ-derived methyl ester): 328.0769. Found: 328.0760.

Step 3

Preparation of [6-Methoxy-2-(4-Methoxyphenyl) benzo[b]thien-3-yl]-[4-[2-(1-Piperidinyl)ethoxy] phenyl] Methanone To a solution of 6-methoxy-2-(4-methoxyphenyl)benzo [b]thiophene-3-carboxylic acid chloride (98.5 mg, 0.296 mmol) in tetrahydrofuran (3 ml) at 2° C. under nitrogen is added dropwise via syringe a solution of 4-[2-(1-piperidinyl) ethoxy]phenylmagnesium bromide (0.48 ml of 0.75 M solution, 0.36 mmol). The resulting mixture is stirred at that temperature for 16 hours, then quenched by addition of methyl alcohol. It is then partitioned between methylene chloride and saturated aqueous ammonium chloride, and the separated organic layer is dried over magnesium sulfate, filtered and concentrated to an oil, which is chromatographed on silica gel (10:5:1 hexanes:dichloromethane:triethylamine) to afford a product-containing fraction, which is further chromatographed on silica gel (10:1:1 hexanes:dichloromethane:triethylamine) to afford title compound as an oil: 88.4 mg (60%). $^1$H NMR spectrum identical to authentic sample. Anal. Calcd. for $C_{30}H_{31}NO_4S$: C, 71.83; H, 6.23; N, 2.79; S, 6.39. Found: C, 71.59; H, 6.32; N, 2.69; S, 6.14.

Step 4

Preparation of 6-Hydroxy-2-(4-Hydroxyphenyl)-3-[4(2-Piperidinoethoxy)benzoyl]benzo[b]thiophene The [6-methoxy-2-(4-methoxyphenyl)benzo[b]thien-3-yl][4-[2-(1-piperidinyl)ethoxy]phenyl] methanone is converted to product by the procedure of Example 2, step 6.

EXAMPLE 6

2-(4-Methoxyphenyl)-3-(4-(2-Piperidinoethoxy) benzoyl)-6Hydroxybenzo[b]thiophene

Step 1

Preparation of 6-Methoxy-2-(4-Methoxyphenyl)-N-Methoxy-N-Methylbenzo[b]thiophene-3-Carboxamide

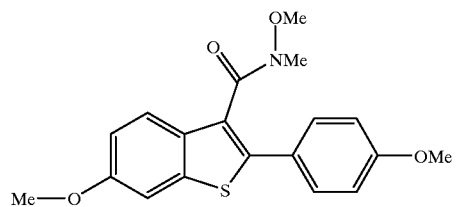

To a slurry of N, O-dimethylhydroxylamine hydrochloride (65.2 mg, 0.674 mmol) in tetrahydrofuran (3 ml) under nitrogen at −78° C. is added sec-butyl lithium (1.0 ml of 1.3 M solution, 1.3 mmol) dropwise via syringe. The resulting slurry is stirred 10 min, then cooling is removed and the mixture allowed to warm to room temperature. A solution of 6-methoxy-2-(4-methoxyphenyl)benzo[b]thiophene-3-carboxylic acid methyl ester (150.3 mg, 0.458 mmol) in tetrahydrofuran (2 ml) is then added via syringe over 2 min. The mixture is stirred for 1 hour, then partitioned between saturated aqueous ammonium chloride and methylene chloride. The organic phase is separated, dried over magnesium sulfate, filtered and concentrated to an oil, which is chromatographed on silica gel(7:3 hexanes:ethyl acetate) to afford, after drying in vacuo, 130.1 mg (0.362 mmol, 80%) of the title compound as an oil: IR (KBr) 2965, 2910, 1648, 1606, 1476, 1250, 1029, 830 cm$^{-1}$; $^1$H NMR (DMSO-d$_6$, 102°) δ7.49 (m, 4 H), 7.04 (m, 3H), 3.85 (s, 3H), 3.81 (s, 3H), 3.45 (br s, 3H), 3.14 (br s, 3H); $^{13}$C NMR (DMSO-d$_6$, 1020) d 164.6, 159.5, 157.2, 138.8, 137.8, 132.2, 128.5, 125.4, 125.2, 122.5, 114.4, 114.3, 105.2, 55.3, 54.9, 33.2. Anal. Calcd. for $C_{19}H_{19}NO_4S$: C, 63.85; H, 5.36; N, 3.92; S, 8.97. Found: C, 63.89; H, 5.36; N, 3.90; S, 8.69.

Step 2

Preparation of [6-Methoxy-2-(4-Methoxyphenyl) benzo[b]thien-3-yl]-[4-[2-(1-Piperidinyl)ethoxy] phenyl] Methanone To a solution of 6-methoxy-2-(4-methoxyphenyl)-Nmethoxy-N-methylbenzo[b]thiophene-3-carboxamide (94.6 mg, 0.265 mmol) in tetrahydrofuran (4 ml) under nitrogen at 5° C. is added dropwise over 2 min via syringe a solution of 4-[2(1-piperidinyl)ethoxy]phenylmagnesium bromide (1.9 ml of 0.71 M solution, 1.35 mmol). The solution is allowed to warm to room temperature, and is stirred for 36 hours, then quenched by addition of saturated aqueous ammonium chloride (5 ml), and partitioned between water and methylene chloride. Following layer separation, the aqueous layer is extracted with additional methylene chloride, and the combined organic layers are dried over magnesium sulfate, filtered, and concentrated to an oil, which is chromatographed on silica gel (5:2:1 hexanes:dichloromethane:triethylamine) to afford a product-containing fraction. This is dissolved in methylene chloride and washed sequentially with 1 N hydrochloric acid and 1 N sodium hydroxide, dried over magnesium sulfate, filtered and concentrated to afford title compound as an oil: 38.3 mg (0.076 mmol, 29%). IR and $^1$H NMR spectra identical to authentic material. Exact mass calcd. for $C_{30}H_{32}NO_4S$: 502.2052. Found: 502.2074.

Step 3

Preparation of 6-Hydroxy-2-(4-Hydroxyphenyl)-3-[4(2-Piperidinoethoxy)benzoyl]benzo[b]thiophene The [6-methoxy-2-(4-methoxyphenyl)benzo[b]thien-3-yl][4-[2-(1-piperidinyl)ethoxy]phenyl] methanone is converted to the title compound by the procedure of Example 2, step 6.

EXAMPLE 7

2-(4-Methoxyphenyl)-3-(4-(2-Piperidinoethoxy)benzoyl)-6-Hydroxybenzo[b]thiophene Step 1

Preparation of 6-Methoxy-2-(4-Methoxyphenyl)benzo[b]thiophene-3-Carboxamide $CONH_2$

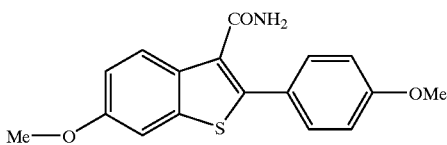

To a solution of ammonia (2 ml) in tetrahydrofuran (10 ml) at −78° C. is added a solution of 6-methoxy-2-(4-methoxyphenyl)benzo[b]thiophene-3-carboxylic acid chloride (0.52 g, 1.56 mmol) in methylene chloride (5 ml). The resulting solution is stirred at −78° C. for 1 hour, then allowed to warm to room temperature and stand for 16 hours. The resulting solid mass is diluted with methylene chloride (20 ml), and partitioned between water and methylene chloride. The lower organic layer, containing suspended solid material, is separated from the aqueous layer and concentrated to afford 460 mg (94%) of title compound as a solid: mp 221.0–222.7° C. IR (KBr) 3419, 3303, 1643, 1617, 1604, 1240, 1035, 805 cm$^{-1}$; $^1$H NMR (CDCl$_3$) δ8.12 (d, 1 H, J=9.0 Hz), 7.53 (d, 2 H, J=8.6 Hz), 7.25 (s, 1 H), 7.05 (dd, J=9, 2.4 Hz), 6.97 (d, 2 H, J=8.6 Hz), 5.49 (br d, 2 H), 3.88 (s, 3 H), 3.86 (s, 3 H). $^{13}$C NMR (DMSO-d$_6$) d 167.6, 160.0, 157.8, 139.6, 138.1, 133.4, 130.0, 129.4, 126.1, 124.0, 115.2, 114.8, 105.4, 56.1, 55.8. Anal. Calcd. for $C_{17}H_{15}NO_3S$: C, 65.16; H, 4.82; N, 4.47; S, 10.23. Found: C, 64.98; H, 4.82; N, 4.66; S, 10.26.

Step 2

Preparation of 6-Methoxy-2-(4-Methoxyphenyl)-3-Cyanobenzo[b]thiophene

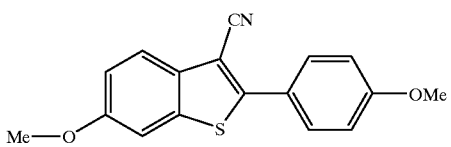

To a slurry of 6-methoxy-2-(4-methoxyphenyl)benzo[b]thiophene-3-carboxamide (0.4488 g, 1.43 mmol) in tetrahydrofuran (20 ml) at 5° C. is added triethylamine (0.5 ml, 3.58 mmol) and trifluoroacetic acid anhydride (0.26 ml, 1.79 mmol). The cooling bath is removed and the reaction allowed to warm to room temperature and stir for 16 hours. The contents are partitioned between water and methylene chloride, and the organic layer is separated, dried over magnesium sulfate, filtered and concentrated to a solid, which is chromatographed on silica gel (9:1 dichloromethane:toluene) to afford 386.9 mg (92%) of title compound as a solid: mp 141.7–142.9° C. IR (KBr) 2985, 2214, 1610, 1498, 1479, 1260, 1033 cm$^{-1}$; $^1$H NMR (CDCl$_3$): δ7.82 (d, 2 H, J=8.9 Hz), 7.81 (d, 1 H, J=8.8 Hz), 7.28 (d, 1 H, J=2.2 Hz), 7.12 (dd, 1 H, J=8.9, 2.2 Hz), 7.02 (d, 2 H, J=8.9 Hz), 3.90 (s, 3 H), 3.88 (s, 3 H); $^{13}$C NMR (CDCl$_3$): d 161.1, 158.5, 155.5, 131.0, 138.5, 133.1, 129.4, 124.3, 123.0, 115.8, 114.7, 104.9, 100.2, 55.8, 55.5. Anal. Calcd. for $C_{17}H_{13}NO_2S$: C, 69.13; H, 4.44; N, 4.74; S, 10.85. Found: C, 68.86; H, 4.66; N, 4.52; S, 10.76.

Step 3

Preparation of 6-Methoxy-2-(4-Methoxyphenyl)-3-[4-[2-(1-Piperidinyl)ethoxy]phenyl]benzo[b]thiophene-3-Methanimine

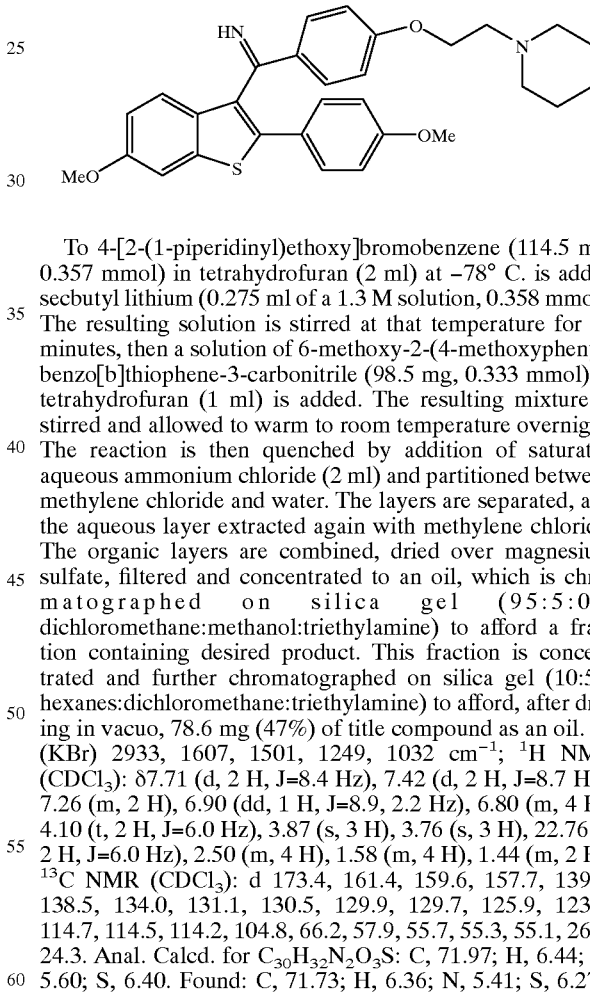

To 4-[2-(1-piperidinyl)ethoxy]bromobenzene (114.5 mg, 0.357 mmol) in tetrahydrofuran (2 ml) at −78° C. is added secbutyl lithium (0.275 ml of a 1.3 M solution, 0.358 mmol). The resulting solution is stirred at that temperature for 30 minutes, then a solution of 6-methoxy-2-(4-methoxyphenyl)benzo[b]thiophene-3-carbonitrile (98.5 mg, 0.333 mmol) in tetrahydrofuran (1 ml) is added. The resulting mixture is stirred and allowed to warm to room temperature overnight. The reaction is then quenched by addition of saturated aqueous ammonium chloride (2 ml) and partitioned between methylene chloride and water. The layers are separated, and the aqueous layer extracted again with methylene chloride. The organic layers are combined, dried over magnesium sulfate, filtered and concentrated to an oil, which is chromatographed on silica gel (95:5:0.2 dichloromethane:methanol:triethylamine) to afford a fraction containing desired product. This fraction is concentrated and further chromatographed on silica gel (10:5:1 hexanes:dichloromethane:triethylamine) to afford, after drying in vacuo, 78.6 mg (47%) of title compound as an oil. IR (KBr) 2933, 1607, 1501, 1249, 1032 cm$^{-1}$; $^1$H NMR (CDCl$_3$): δ7.71 (d, 2 H, J=8.4 Hz), 7.42 (d, 2 H, J=8.7 Hz), 7.26 (m, 2 H), 6.90 (dd, 1 H, J=8.9, 2.2 Hz), 6.80 (m, 4 H), 4.10 (t, 2 H, J=6.0 Hz), 3.87 (s, 3 H), 3.76 (s, 3 H), 22.76 (t, 2 H, J=6.0 Hz), 2.50 (m, 4 H), 1.58 (m, 4 H), 1.44 (m, 2 H); $^{13}$C NMR (CDCl$_3$): d 173.4, 161.4, 159.6, 157.7, 139.9, 138.5, 134.0, 131.1, 130.5, 129.9, 129.7, 125.9, 123.8, 114.7, 114.5, 114.2, 104.8, 66.2, 57.9, 55.7, 55.3, 55.1, 26.0, 24.3. Anal. Calcd. for $C_{30}H_{32}N_2O_3S$: C, 71.97; H, 6.44; N, 5.60; S, 6.40. Found: C, 71.73; H, 6.36; N, 5.41; S, 6.27.

Step 4

Preparation of [6-Methoxy-2-(4-methoxyphenyl)benzo[b]thien-3-yl] [4-[2-(l-piperidinyl)ethoxy]phenyl] methanone To a solution of 6-methoxy-2-(4-methoxyphenyl)-3-[4-[2-(1-piperidinyl)ethoxy]phenyl]benzo[b]thiophene-3- methanimine (8.6 mg, 0.017 mmol) in tetrahydrofuran (2 ml) is added 1 N hydrochloric acid (2 ml) and the resulting solution is heated to reflux for 16 hours. The reaction mixture is then partitioned between methylene chloride and 1 N sodium hydroxide, and the organic layer separated, dried over magnesium sulfate, concentrated and chromatographed on silica gel (5:1:1 hexanes:dichloromethane:triethylamine) to afford 4.0 mg (46%) of title compound as an oil after drying in vacuo. $^1$H NMR spectrum identical to authentic sample. Exact mass calcd. for $C_{30}H_{32}NO_4S$: 502.2026. Found: 502.2052.

Step 5

Preparation of 6-Hydroxy-2-(4-Hydroxyphenyl)-3-[4-(2-Piperidinoethoxy)benzoyl]benzo[b]thiophene The [6-Methoxy-2-(4-methoxyphenyl)-benzo[b]thien-3-yl] [4-[2-(1-piperidinyl)ethoxy]phenyl] methanone is converted the title compound by the procedure of Example 2, step 6.

We claim:

1. A compound of formula V

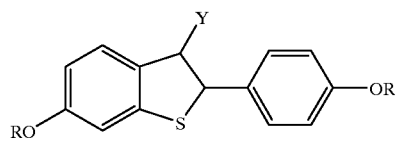

V wherein:
R at each occurrence is independently a hydroxy protecting group;
Y is —$CO_2R^1$, —CO-halo, —CONMe(OMe), —$CONH_2$, or cyano; and.

2. A compound according to claim 1 wherein said hydroxy protecting group is $C_1$-$C_4$ alkyl.

3. A compound according to claim 2 wherein said hydroxy protecting group is methyl.

4. A compound of formula IX

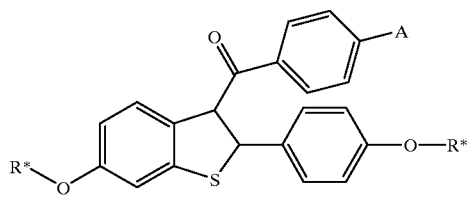

IX wherein:
A is hydroxy, halo, nitro, $C_1$-$C_4$ alkoxy, —O—$(CH_2)_2$-halo, or —O—$(CH_2)_2$—$NR^2R^3$;
$R^*$ is independently at each occurrence a hydroxy protecting group or hydrogen; and
$R^2$ and $R^3$ are independently $C_1$-$C_4$ alkyl, or combine to form, together with the nitrogen atom to which they are attached, a pyrrolidinyl, piperidinyl, morpholino, or hexamethyleneimino ring; or a pharmaceutically acceptable salt or solvate thereof.

5. A compound according to claim 4 wherein A is —O—$(CH_2)_2$—$NR^2R^3$ or hydroxy.

6. A compound according to claim 5 wherein $R^2$ and $R^3$ combine to form, together with the nitrogen atom to which they are attached, a piperidinyl ring.

7. A process for preparing a compound of formula IX

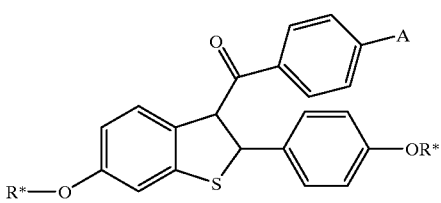

IX wherein:
A is hydroxy, halo, nitro, $C_1$-$C_4$ alkoxy, —O—$(CH_2)_2$-halo, or —O—$(CH_2)_2$—$NR^2R^3$;
$R^*$ at each occurrence is independently a hydroxy protecting group or hydrogen; and
$R^2$ and $R^3$ are independently $C_1$-$C_4$ alkyl, or combine to form, together with the nitrogen atom to which they are attached, a pyrrolidinyl, piperidinyl, morpholino, or hexamethyleneimino ring;
or a pharmaceutically acceptable salt or solvate thereof, which comprises: condensing a compound of formula Vg

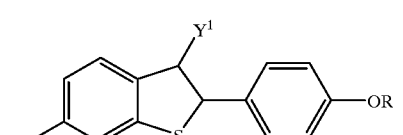

Vg wherein:
R at each occurrence independently is a hydroxy protecting group; and
$Y^1$ is —$CO_2R^1$, —CO-halo, —CONMe(OMe), or cyano; with a compound of formula VI

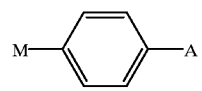

VI wherein M is hydrogen, lithium, magnesium chloride, magnesium bromide, or magnesium iodide; with the proviso that when M is hydrogen, then Y is —CO-halo; in the presence of a Lewis acid catalyst.

8. A process according to claim 7 wherein A is hydroxy or —O—$(CH_2)_2$—$NR^2R^3$.

9. A process for preparing a compound of formula X

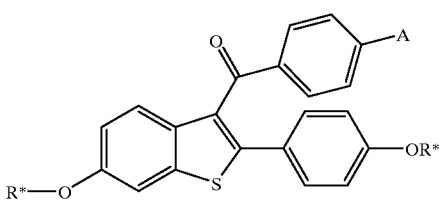

X wherein:
A is hydroxy, halo, nitro, $C_1$-$C_4$ alkoxy, —O—$(CH_2)_2$-halo, or —O—$(CH_2)_2$—$NR^2R^3$;

R* at each occurrence is independently a hydroxy protecting group or hydrogen; and R² and R³ are independently C₁-C₄ alkyl, or combine to form, together with the nitrogen atom to which they are attached, a pyrrolidinyl, piperidinyl, morpholino, or hexamethyleneimino ring; or a pharmaceutically acceptable salt or solvate thereof, which comprises: reacting a compound of formula IX

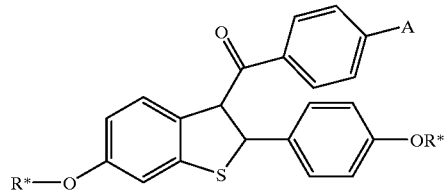

IX with a suitable oxidizing reagent.

10. A process for preparing a compound of formula Vc:

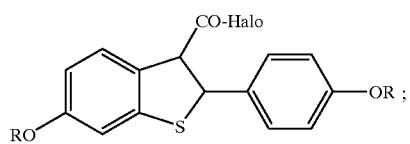

Vc wherein R is independently at each occurrence a hydroxy protecting group; which comprises: (a) reacting a compound of formula IV:

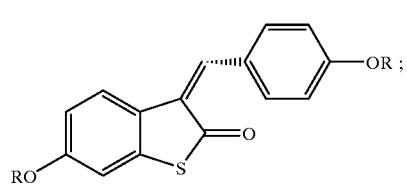

IV with a lower alcohol in the presence of a suitable base to form a compound of formula Va:

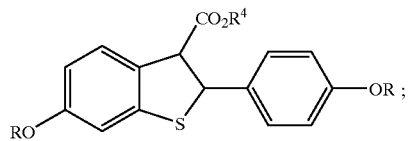

Va wherein R⁴ is C₁-C₄ alkyl; and (b) converting the product of (a) to the corresponding carboxylic acid of formula Vb:

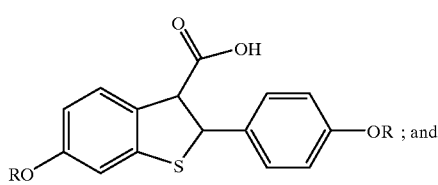

Vb (c) reacting the product of (b) with a halogenating reagent.

11. A process according to claim 10 which further comprises reacting a compound of formula Vc with a compound of the formula HNMe(OMe) in the presence of a suitable base to prepare a compound of formula Vd:

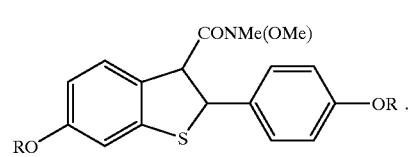

Vd

12. A process according to claim 10 which further comprises reacting a compound of formula Vc with ammonia to prepare a compound of formula Ve

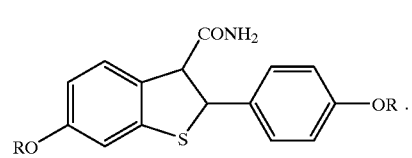

Ve

13. A process according to claim 12 which further comprises reacting a compound of formula Ve with a suitable base and trifluoroacetic anhydride to prepare a compound of formula Vf

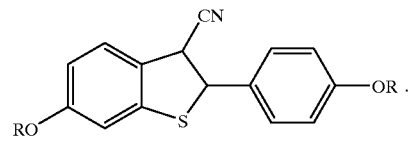

Vf

* * * * *